United States Patent
Westbrook et al.

[19]

[11] Patent Number: 6,067,844

[45] Date of Patent: May 30, 2000

[54] NONDESTRUCTIVE METHOD FOR DETECTION OF DEFECTS AND THE CONDITION OF LINERS IN POLYMER-LINED PIPES AND EQUIPMENT

[75] Inventors: Paul Alfred Westbrook, Richmond; Roderick Leonard Shulver, The Woodlands, both of Tex.

[73] Assignee: Shell Oil Company, Houston, Tex.

[21] Appl. No.: 08/911,684

[22] Filed: Aug. 15, 1997

[51] Int. Cl.[7] ............................. G01M 3/08; G01N 15/08
[52] U.S. Cl. ............................. 73/40.5 R; 73/38
[58] Field of Search ............................. 73/40.5 R, 40.7, 73/49.2, 38, 40, 49.1

[56] References Cited

U.S. PATENT DOCUMENTS

| | | | |
|---|---|---|---|
| 3,299,417 | 1/1967 | Sibthorpe | 340/605 |
| 3,339,415 | 9/1967 | Wild | 73/40.5 |
| 3,546,634 | 12/1970 | Roy | 73/38 |
| 4,450,711 | 5/1984 | Claude | 73/40.5 R |
| 4,596,133 | 6/1986 | Smalling et al. | 73/24 |
| 4,736,623 | 4/1988 | Brown et al. | 73/49.2 |
| 4,754,650 | 7/1988 | Smalling et al. | 73/861.28 |
| 4,761,553 | 8/1988 | Juravic | 250/298 |
| 4,918,975 | 4/1990 | Voss | 74/40.7 |
| 5,072,622 | 12/1991 | Roach et al. | 73/40.5 R |
| 5,077,385 | 12/1991 | Gerlowski et al. | 528/392 |
| 5,157,960 | 10/1992 | Brehm et al. | 73/38 |
| 5,301,538 | 4/1994 | Recla | 73/40.5 F |
| 5,351,524 | 10/1994 | Lanham | 73/40.5 R |
| 5,375,457 | 12/1994 | Trapp | 73/40.7 |
| 5,440,918 | 8/1995 | Oster | 73/40.5 R |
| 5,458,258 | 10/1995 | White et al. | 220/589 |
| 5,730,472 | 3/1998 | Krause et al. | 285/21.1 |

*Primary Examiner*—Hezron Williams
*Assistant Examiner*—Jay L. Politzer
*Attorney, Agent, or Firm*—Kim Muller

[57] ABSTRACT

The semi-permeable characteristics of polymeric liners may be used to characterize defects, if present, in loose liners contained inside piping and equipment. The use of polymer-lined equipment is common in the chemical, refining and other industries where the polymeric liner offers excellent chemical resistance and the outer shell gives the required strength and rigidity. Permeability characteristics of liners are investigated with particular reference to volatile process gasses and/or process-soluble tracer gasses. The resulting data are used to establish nondestructive testing techniques for evaluating the integrity of lined equipment during normal operation where a mass spectrometer equipped with a sampling probe is used as the sampling and sensing devices. Real-time data is compared to characteristic data, obtained under laboratory conditions, on a membrane of the polymer from which the liners are made. Acceptance or rejection of the equipment is determined by such comparison. Equipment containing defective liners may be removed from service before the defect causes a leak.

14 Claims, 6 Drawing Sheets

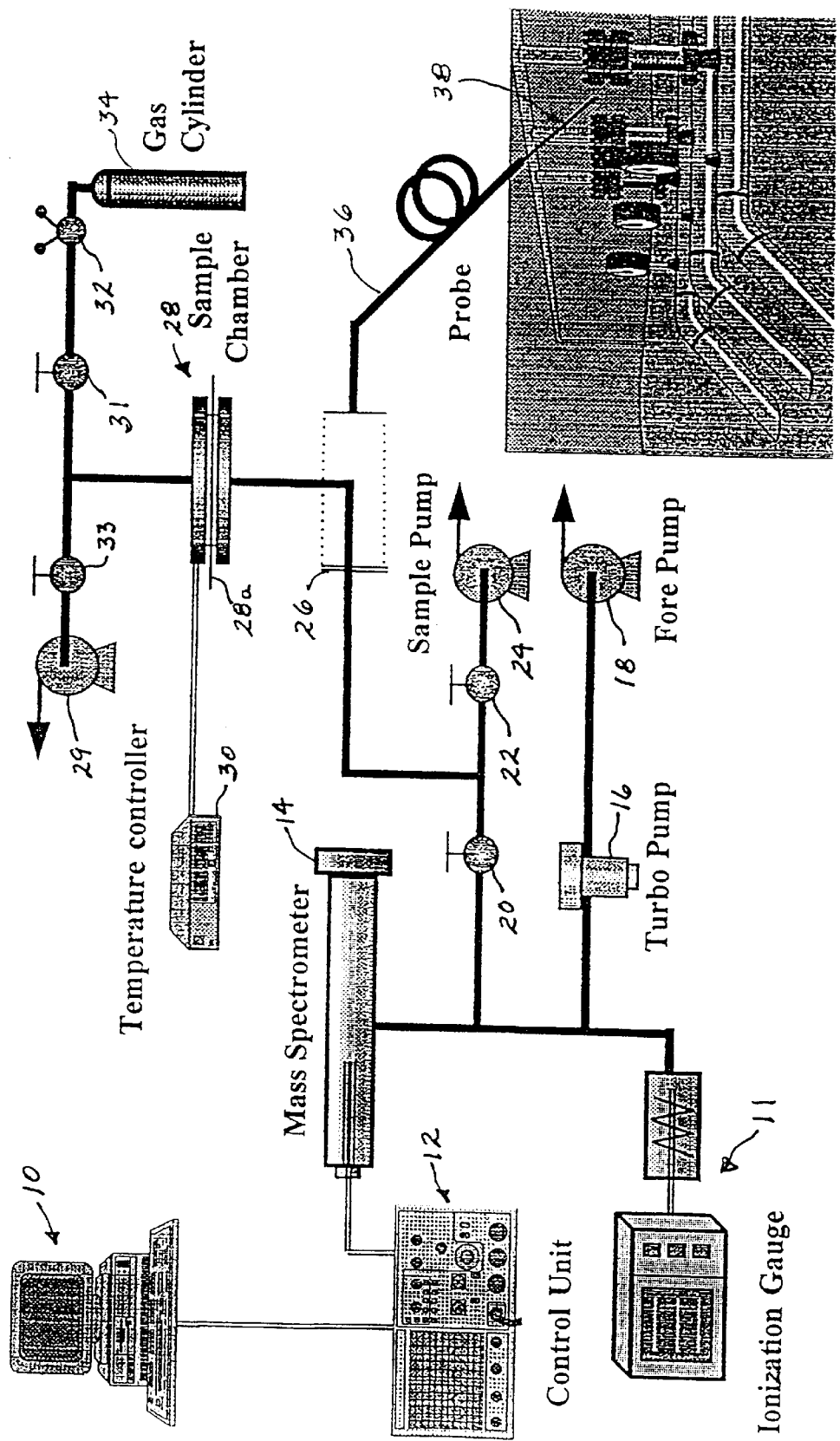
FIGURE 2 –

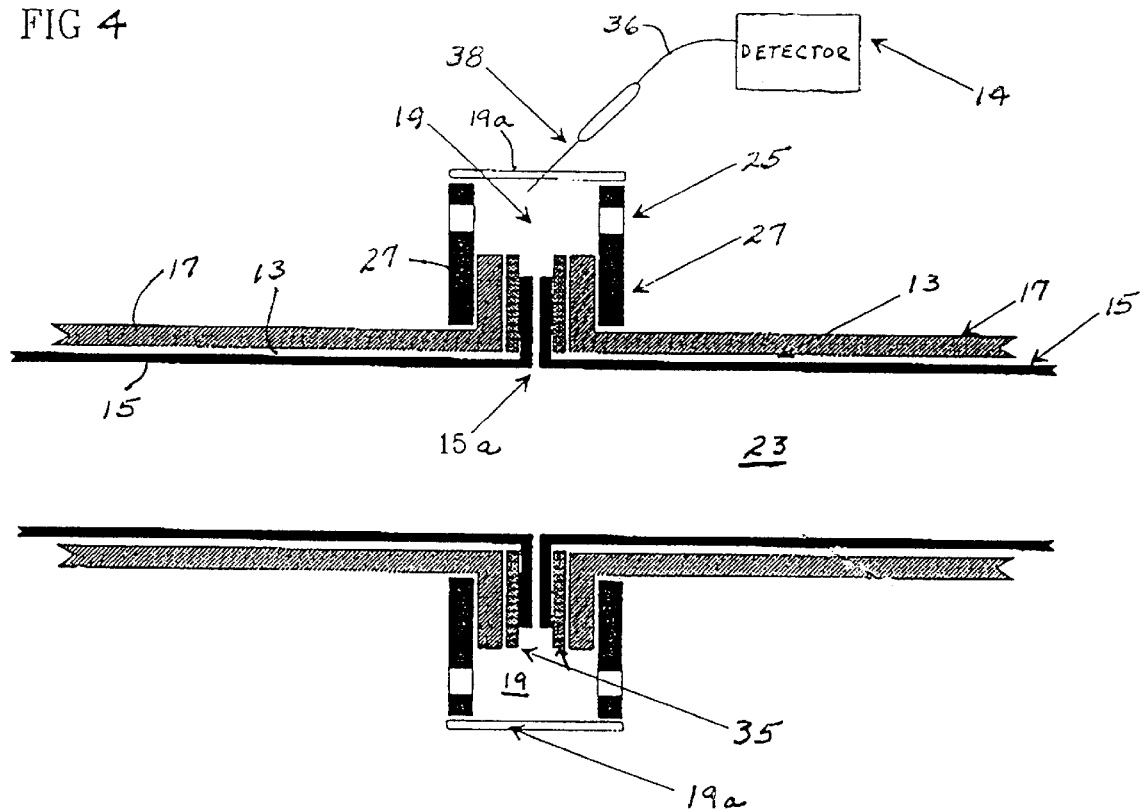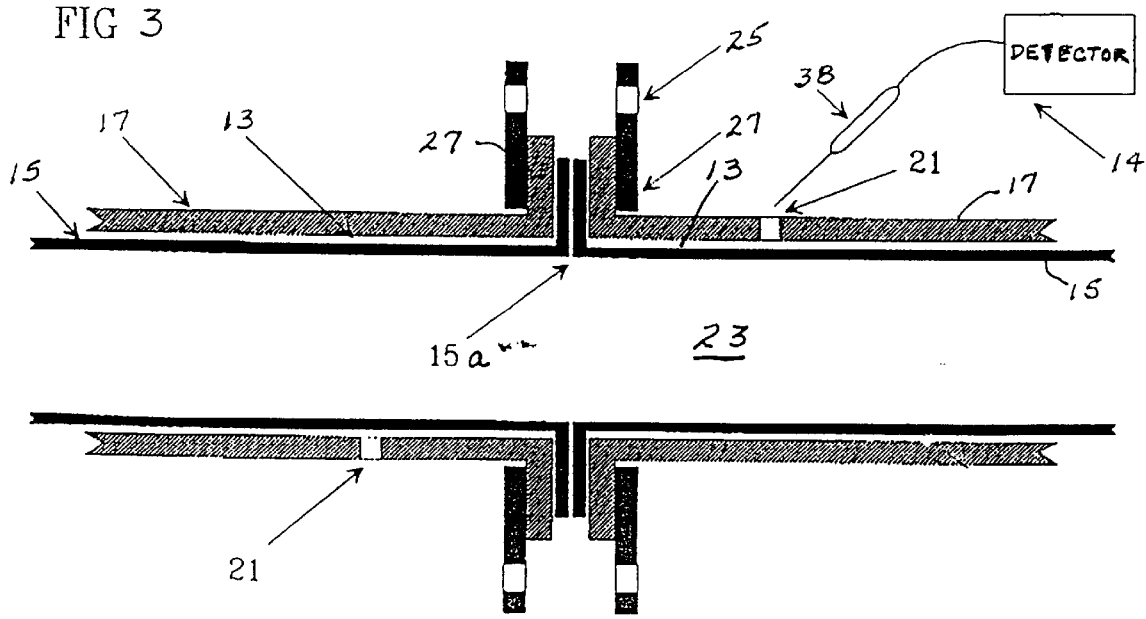

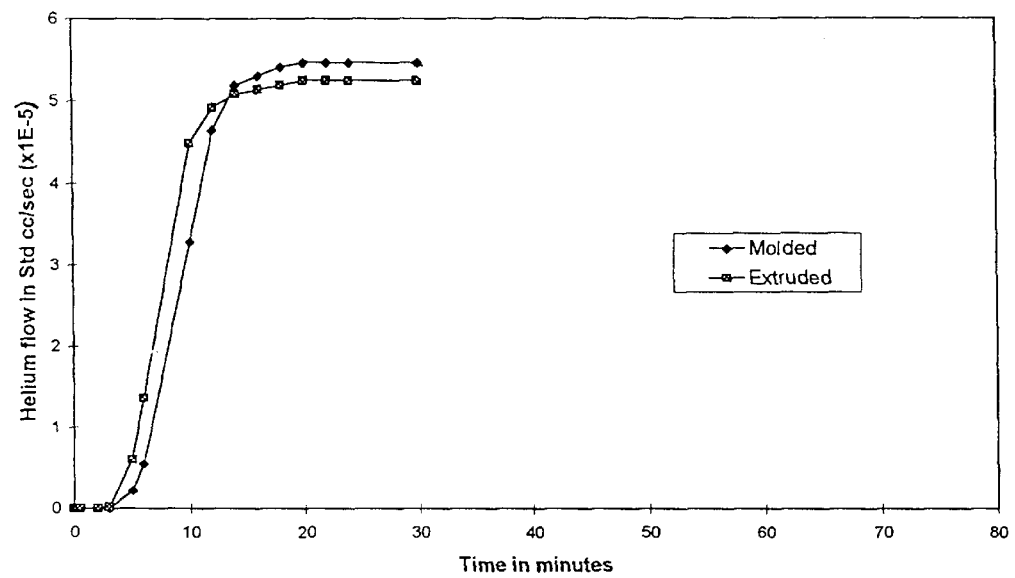

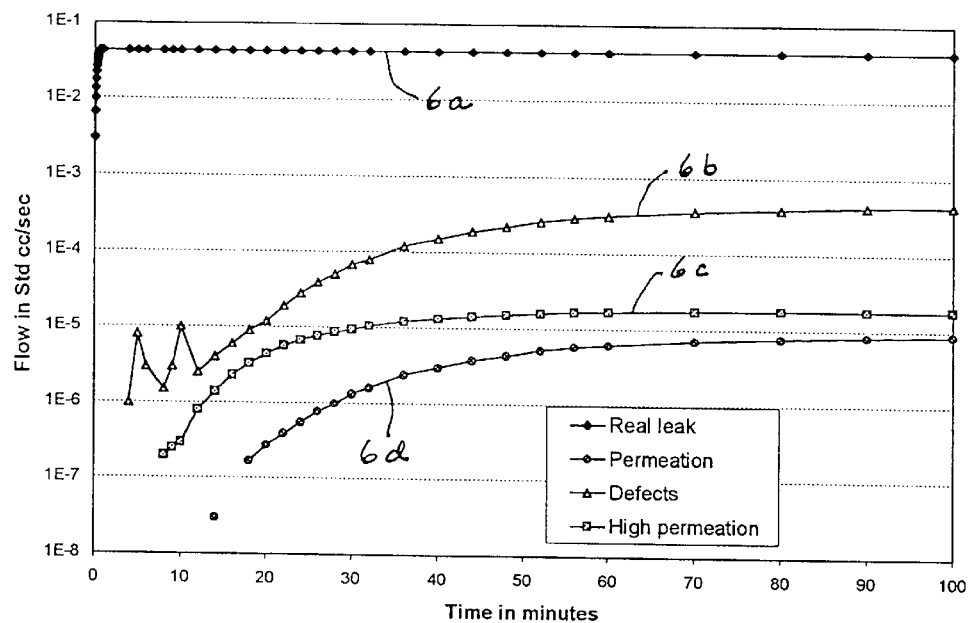

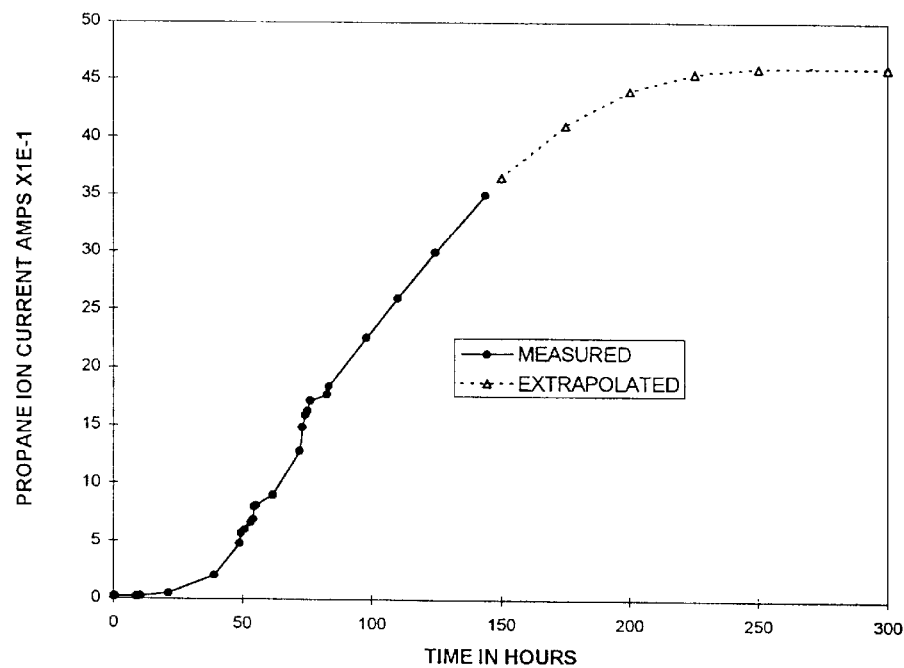

NONDESTRUCTIVE METHOD FOR DETECTION OF DEFECTS AND THE CONDITION OF LINERS IN POLYMER-LINED PIPES AND EQUIPMENT

BACKGROUND OF THE INVENTION

1. Field of the Invention

This invention relates to an improved method of, and device for, on-line and out-of-service inspection and evaluation of internal, loose polymeric liner in piping and equipment. In particular, a nondestructive method for determination of the presence or absence of defects is accomplished, before actual leakage occurs, by an in-situ measurement of vapor permeability through the liner itself.

2. Description of the Prior Art

Plastic liners in process equipment are usually intended for corrosion protection of the underlying structural shell. Liners may become defective due to manufacturing and/or in-service related considerations. Liner defects such as environmentally assisted cracking, blistering, erosion, manufacturing defects and other defects have been observed in lined piping and equipment. While these defects may not present an immediate leakage symptom, they may limit the remaining useful life of the asset.

Conventional nondestructive testing (NDT) techniques such as visual inspection of the exterior shell, radiography, eddy current, ultrasonic, microwave and other methods cannot reliably assess the character of defects in a loose, plastic liner contained inside a structural shell before actual leakage occurs. Several methods and devices have been disclosed for detection of leaks in lined piping and/or double-walled piping. However, no method has been disclosed to nondestructively detect defective liners which pose an increased risk of loss of integrity.

U.S. Pat. No. 5,375,457 to Trapp (Dept. of Energy) discloses a method and device for detecting the location of leaks along a wall or piping system, preferably in double-walled piping. The apparatus comprises a sampling probe, a rigid cord such as a length of tube attached to the probe on one end and extending out of the piping with the other end, a source of pressurized air and a source of helium. The method comprises guiding the sampling probe into the inner pipe to its distal end, purging the inner pipe with pressurized air, filling the annulus defined between the inner and outer pipe with helium, and then detecting the presence of helium within the inner pipe with the probe as it is pulled back through the inner pipe. The length of the tube at the point where a leak is detected determines the location of the leak in the pipe.

U.S. Pat. No. 5,301,538 to Recla (Teledyne Industries) discloses a method and apparatus in which dual sensor detector tube systems are installed along the path length of a pipeline, storage tank, or other fuel system to be monitored for leaks. One sensor detector tube system is constantly evacuated and passed through a sensor detector to test for presence of vapors or gaseous indications of large leaks. Concurrently, the other sensor detector tube system is permitted to lie dormant for a predetermined period to absorb and receive vapors or gases from medium-to-small leaks that are too small to be detected by the continuous air flow system of the first tube. Periodically the flow of the two-sensor detector tube system is interchanged to evacuate the dormant tube which then becomes the continuously aspirated system. Signal output from the sensor detectors provide data to the control alarm system which compares concentration profiles of current on-going tests with recorded profiles of prior tests, and any significant deviation is recognized as a problem, sounding an alarm. The system provides direct data for location of small leaks, with significant indications for location of large leaks.

U.S. Pat. No. 5,072,622 to Roach et al discloses a pipe system comprising at least one lined pipe section. This lined pipe section comprises an outer pipe having an exterior wall, a thermoplastic liner having an exterior surface flush and in tight engagement with the interior wall of the outer pipe, and at least one groove located in the exterior surface. The groove and the interior wall of the outer pipe define at least one passageway at the interface of the interior wall of the outer pipe and the exterior surface of the liner with which a leak detector may be associated. This allows detection of leakage due to holes or perforations created by corrosion or other means in the outer pipe or due to cracks or holes in the inner liner. This invention therefore provides an effective dual containment system since the integrity of both the inner liner and the outer pipe may be monitored.

U.S. Pat. No. 4,450,711 to Claude (Technigaz, France) discloses a pipeline for conveying a fluid submerged in an ambient fluid medium which has an inner conveying tube surrounded by an outer tube radially spaced from the inner tube and defining a continuous annular space therebetween. A leak conductor communicating with a leak collector and surrounding the inner conveying tube conducts leaks of conveyed fluid to the leak collector. The leak collector has a reduced cross-section and is divided into adjacent sections isolated in a fluid-tight manner relative to each other and extending throughout the length of the tube. Each of the sections has at least a single valve automatically opened by predetermined pressure of the conveyed fluid leaks for providing communication with the annular space surrounding the inner tube. A leak detecting system in the annular space includes a sweeping device for sweeping the annular space with an auxiliary fluid and an analyzing device for analyzing the composition of the auxiliary fluid at one accessible end of the pipeline and at spaced locations along the pipeline. A warning device connected to the analyzing device is operable when the analyzing device indicates a predetermined pressure.

Each of the above-mentioned patents teaches methods and devices for determining the presence of leaks in lined piping and equipment or double walled piping. Since liners in process equipment are often used to protect the structural shell from highly corrosive media, loss of liner integrity may cause sudden leakage which is accompanied by considerable risk of health, safety and environmental consequences. As such, leak detection has little value for lined equipment in highly corrosive services. Therefore, a safe, cost-effective method is needed to identify suspect and/or defective liners substantially before leakage is imminent.

The present invention teaches that the semi-permeable membrane properties of the polymeric liner provides a rational basis for its inspection. The natural permeation behavior of volatile gasses is monitored and the measured quantity is compared against expected values for virgin materials. Any change of liner permeability may be related to changes in its physical condition. Any observed changes in membrane properties of the liner provides a basis for deducing certain aspects of its integrity.

SUMMARY OF THE INVENTION

This method is concerned with detecting defective liners before a defect has grown to the extent where an actual leak occurs. The condition of plastic-lined pipe is assessed by monitoring the fugitive emission of volatile process gasses and/or soluble tracer gasses both at the annulus vents and at gasketed or ungasketed flanges. Volatile process or tracer gasses are known to diffuse through polymeric liners by a process called permeation. A measured liner permeability significantly above known or expected levels is indicative of defective liners. Conversely, a measured liner permeability significantly below known or expected levels represents an improvement in permeation resistance. Such an improvement in permeation resistance by a liner is, perhaps, indicative of restricting microporosities in the liner by impurities and is not part of this invention. Because nonleaking defects in liners, such as cracking, thinning, blistering, and others often produce excess permeation which is orders of magnitude above the expected baseline permeation from virgin liners, this method effectively detects these kinds of defects even if the intrinsic permeability of the liner is reduced by restricted micropores. The detection of actual leaks by viscous flow of gasses in through-wall defects is not part of this invention. It will also be appreciated that other suitable detectors utilizing manometric, coulometric, thermal conductivity and other principles may also be applied. The preferred method and apparatus requires a system, utilizing a detector such as a mass spectrometer residual gas analyzer, or a mass spectrometer specifically tuned to an individual gas, and a sampling probe. The apparatus can detect, in-situ, fugitive emission of volatile gasses. Emissions are detected with high sensitivity and resolution and low turnaround time.

The permeation testing procedures discussed herein constitute a cost-effective method to provide quantitative information on the integrity of plastic-lined pipe spools in quality control testing and in actual operation. The ability to detect volatile process gasses or soluble tracer gasses on-line enables inspection of lined pipe spools during normal operation of the unit. These methods provide for 100 percent coverage and rapid feedback on excessive flange emission and liner permeation such that preventive maintenance activities may be prioritized.

BRIEF DESCRIPTION OF THE DRAWINGS

FIG. 2 is a schematic diagram of measurement apparatus.

FIG. 3 is a schematic diagram of the apparatus used for detecting gas at vent holes.

FIG. 4 is a schematic diagram of the apparatus used for detecting gas at flanges.

FIG. 5 shows curves showing helium permeation through two PTFE lines.

FIG. 6 presents curves showing a comparison of leaks, permeation and defects in lined pipe.

FIG. 7 is a curve showing propane permeation through PTFE at 174° F.

THEORETICAL BACKGROUND OF VISCOUS AND MOLECULAR FLOW

Dimensions for Vapor Transport

Figure 1:
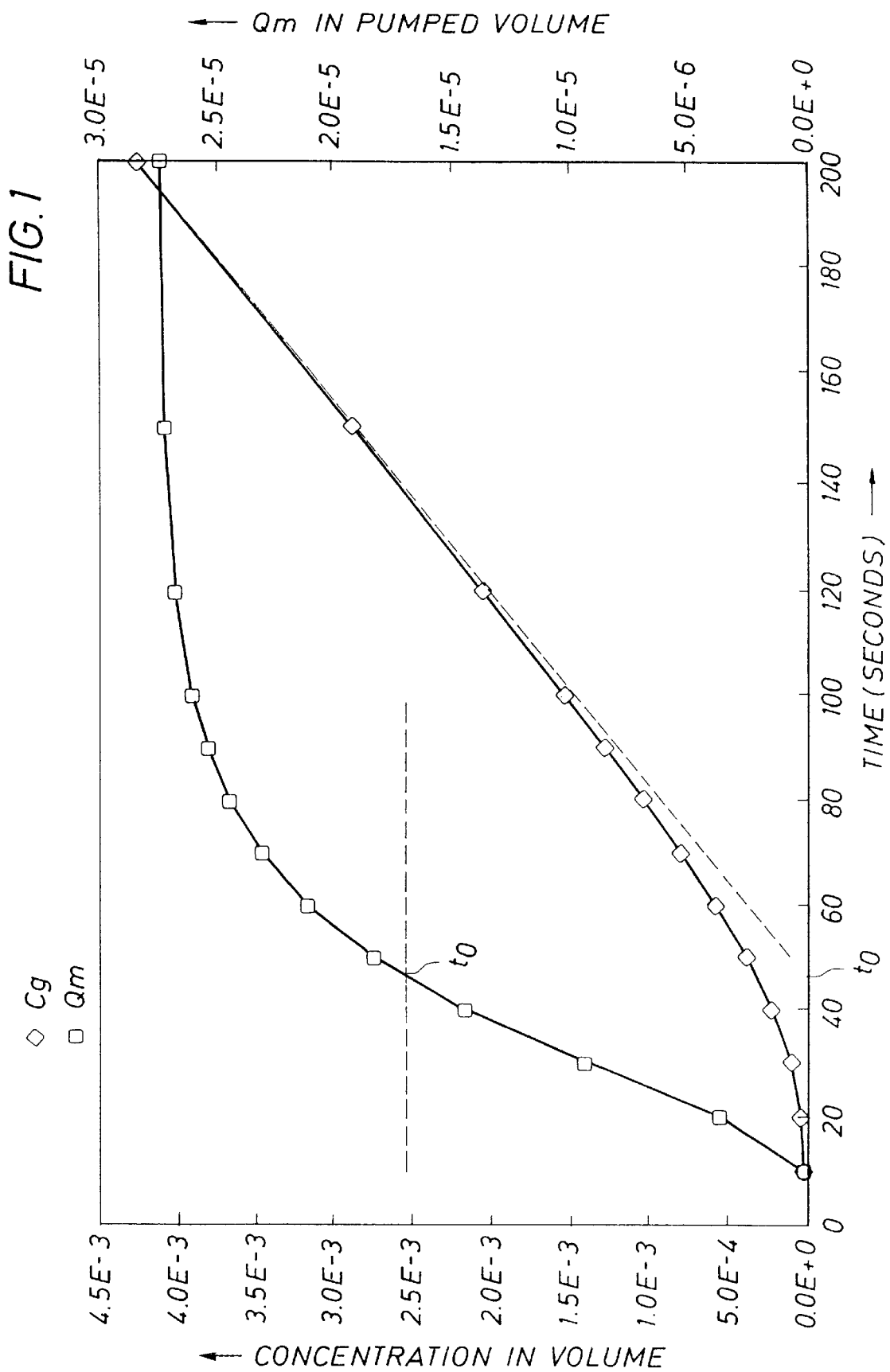
FIG. 1 shows curves for helium permeation through PTFE at 95° F.

When discussing permeation rates, it is important to note that any emission should always refer to units of mass flow. For vapors, the appropriate emission rate unit is pressure multiplied by volume per unit of time. If the composition and temperature of the gas are known, the actual mass emission can be computed from the Ideal Gas Law. Thus, a vapor emission rate is proportional to the isothermal mass flow of a given gas.

The petrochemical industry often uses emission rate units as standard cubic feet per year, std. $ft^3$/yr. SI units are Pascal cubic meters per second, $Pa*m^3$/sec. Preferred and commonly used units are standard cubic centimeters per second, std. $cm^3$/sec. The standard volumetric unit refers to a volume of gas at one atmosphere absolute pressure and zero degrees Centigrade.

Mechanisms of Vapor Transport

There are two types of vapor transport, viscous flow and molecular flow. If the leak pathway is greater than the mean free path of the solute molecule, then viscous flow will govern. Viscous flow may be expected from a through-wall crack, hole or other defect, for example and is fundamentally different than permeation. If the leak pathway is less than the mean free path of the solute molecule, then molecular flow will govern. Molecular flow often occurs in vacuum systems and is the dominant mechanism of solute permeation in polymers.

Permeation

Consider first the linear permeation of a solute through a membrane into a collection volume. Fick's law describes the linear permeation rate (P) of a solute through a membrane as the product of the solubility (S) and the diffusivity (D) of the solute.

$$P = S*D \tag{1}$$

The one-dimensional differential form of Fick's law may be expressed as follows:

$$\frac{\partial C}{\partial t} = -D\frac{\partial^2 C}{\partial x^2} \tag{2}$$

where C is the concentration of solute at any time, t, and at any point x within the membrane thickness. Assume that an infinite (area) slab geometry is used and that the slab is initially free of solute. Further assume that the concentration of solute at the inside surface is constant, $C_o$, and the concentration of solute at the outside surface is zero but builds with time as the solute collects. The resulting equation for the solute concentration ($C_g$) collecting in a non-vented fixed volume, V, as a function of time, t, is written as:

$$C_g = [t-t_o]C_o D\, A/L\, V \tag{3}$$

where:

$$t_o = L^2/6D, \tag{3a}$$

A=the area of the membrane and
L=the total thickness of the membrane.

Eq. 3 is plotted schematically in FIG. 1 on the left ordinate as $C_g$. Determination of the onset time $t_o$ allows one to compute the diffusivity D.

Alternatively, if the collection volume is continually evacuated, for example by a vapor sampling device such as a mass spectrometer, then the total mass flow $Q_m$ through the membrane is given as:

$$Q_m = VdC_g/dt = \tag{4}$$
$$SVdP/dt = C_0 DA\bigg/L\bigg[1 + 2\sum_{n=1}^{\infty}\cos(n\pi)*\exp(-(n\pi/L)^2 Dt)\bigg]$$
$$[1 - \exp(-S_V t/V)]$$

where $S_v$ is the evacuation rate, or pump speed and $C_o$ is the concentration of solute at x=0. Eventually the pressure, or concentration, reaches a steady state value whereby the mass flow rate through the spectrometer equals the permeation rate of the membrane. This behavior is plotted as the right ordinate of FIG. 1 as $Q_m$. Now, P is determined from $Q_m$ and the geometry of the sample. If desired, S is subsequently calculated from P and D using Fick's law, Eq. (1).

In general, D depends upon the inverse square root of the molecular mass of the diffusing solute whereas S depends upon a binary interaction parameter that is related to the enthalpy of mixing of polymer and solute. Therefore a high permeability may be observed with either small, volatile solutes or with solutes that strongly associate with the matrix material or both.

Effect of Temperature on Permeability Coefficient

Permeation of vapors through polymers has been shown to be a thermally activated process. Therefore an Arrhenius form may be adopted to correlate the observed permeability increase with temperature as suggested below:

$$P_T/P_{To} = \exp\{-(E/R)(1/T - 1/T_o)\} \tag{5}$$

where:

E is an activation energy constant,

R is the universal gas constant,

T is temperature in °K, and $T_o$ is the reference temperature in °K.

Viscous Flow

In contrast to molecular flow, the isothermal mass flow rate of a laminar viscous flow of compressible gas is given by the following equation:

$$Q_v = (\Gamma/2\mu)[(P_1^2 - P_2^2)/L]^{1/2} \tag{6}$$

where $Q_v$ is the viscous mass flow rate, $\Gamma$ is a dimensional constant related to the geometry of the pathway, $\mu$ is the fluid viscosity, $P_1^2$ and $P_2^2$ are the squares of the upstream and down stream pressures respectively, and L is the length of the leak path. Thus in viscous flow, die mass flow rate of vapor is proportional to the square root of the difference in the squares of the pressures across the membrane. This is contrasted to molecular flow by permeation, which is proportional to the difference in pressures to the first power, as was shown in Equation 4. R. H. Perry and C. H. Chilton, Eds., *Chemical Engineers' Handbook*, 5th ed., McGraw-Hill, New York (1973) pg. 5–26.

Detection of Gasket Surface Leakage

Now consider viscous flow associated with leakage at a gasket surface. Of course, turbulent flow is also possible; however, one may expect a turbulent gas flow to exhibit positive indications of fluid leakage as well. In either case, a gasket surface may be inspected for integrity by an established method. For flange emission rate measurements, a total allowable emission rate of 2.0×10⁻⁵ mg/sec (of helium) per millimeter of pipe diameter was used. Experience has shown that helium emission on lined pipe with gasket surfaces in good condition may be readily sealed to meet this criterion simply by tightening the flange bolts to 150 percent of the manufacturer's recommended bolt torque value.

DESCRIPTION OF THE PREFERRED EMBODIMENTS

Although the discussion refers to lined pipe, it will be appreciated that the invention may also be directed to other equipment such as vessels, pumps, valves, fittings, etc. Accordingly, the invention provides a method for detecting a greater than anticipated permeation rate of a vapor through the liner in a portion of lined pipe. The outer container of the lined pipe or equipment may be metallic, fiber-reinforced or any other material. The vapor may be a process vapor or a process-soluble tracer gas injected into the process. The vapors are then detected at suitably positioned vent holes (see FIG. 3), or at a flange connection (see FIG. 4) by means of a suitable detector for the gas. The vapor that is used for the permeation analysis should be stable or only react minimally with either the atmospheric constituents or other elements and materials present. Suitable vapors include, but are not limited to: helium, hydrogen, neon, argon, methane, ethane, ethylene, propane, propylene and sulfur hexafluoride. The leak sampling detector should be suitable for the component selected and may take the form of a hydrocarbon analyzer or a mass spectrometer with a resolution adequate for measuring the component selected. The sampling detector may also employ a permeable membrane.

Use of mass spectrometry has been argued to be a more effective technique to detect permeating vapors than the use of manometric or coulometric devices. The mass spectrometry technique was selected for its speed, versatility, sensitivity and resolution.

FIG. 2 is a schematic diagram which shows the basic components associated with the apparatus used for laboratory characterization of membrane materials and subsequently for field testing. The object of the laboratory experiment is to characterize the polymer and the gas of interest, i.e., to obtain the diffusion characteristics of the gas through a polymer membrane 28a. To obtain reference data, the sample chamber 28 is connected to the test connection 26. With valves 31 and 33 open, vacuum pump 29 evacuates the line between gas regulator 32 and the sample chamber 28. Then, with valve 33 closed, a gas is introduced from the gas cylinder 34 through regulator 32 and valve 31, onto the high pressure side of the membrane 28a in sample chamber 28. The high pressure side of the membrane is exposed to whatever gas is in the cylinder 34 and at any desired pressure. A temperature controller 30 controls the temperature of the sample chamber 28. On the downstream side of the membrane 28a a high vacuum is applied at test connection 26 by rotary vane roughing pump 18 and a turbomolecular pump 16. In the laboratory mode, valve 20 is open and valve 22 is closed. The solute gas diffuses through the membrane 28a and is sampled by the mass spectrometer 14. The mass spectrometer 14 measures the quantity of the diffusing gas which is found downstream of the membrane 28a as a function of time. An ionization gauge 11 provides an independent measure of the total system pressure. The computer 10 (which may be, e.g., a 386 or equivalent) is used to record data from the control unit 12 (which may be an Inficon Residual Gas Analyzer) for the mass spectrometer 14. The quantity of solute diffusing through the membrane 28a is measured as a function of time giving a characteristic curve (similar to FIG. 1) which is used to deduce the transport properties; those transport properties being the solubility S, the diffusivity D and the permeability P.

Once the permeability of the solute through the polymer has been measured, an expected mass flow $Q_m$ of the solute of given partial pressure through any pipe liner of given dimensions can be computed. The expected mass flow is computed from the following equation:

$$Q_m = P A \Delta p / L \tag{7}$$

where $\Delta p$ is the change in partial pressure across the pipe liner thickness.

For quality control and field tests, the laboratory equipment 28–34 are removed from the test connection 26 and replaced with a sampling probe 38 having a capillary restriction and connected to a flexible hose 36 which can be, for example, 300 feet long. In this mode, valve 22 is open. Air is used as a carrier gas and is aspirated through the sampling probe 38, the hose 36 and out the sample pump 24. Pump 16 and 18 continue to draw a vacuum. Whatever process gases are permeating through the liner or leaking through the flange are captured by the probe 38. Valve 20 is partially open creating a pressure drop across it and a net flow into the mass spectrometer 14. The quantity of permeant being sampled is measured by concentration in the mass spectrometer 14. A calibration device (not shown) comprising a standard reference leak, which is $1 \times 10^{-5}$, std. $cm^3$/sec, is used to calibrate the field apparatus.

FIG. 4 is a schematic sectional view of a fragmentary portion of two lined pipes 17 flanged together and carrying process gas 23, the vent for the annular space 13 being by means of the flanges 27. The flanges 27 are secured to each other by means of bolts (not shown) through bolt holes 25. The drawing illustrates the use of a detector e.g., mass spectrometer 14 equipped with a sampling probe 38 for measuring the mass flow $Q_m$ of gas permeating through the liner 15 or around the connecting flanges 27. This data allows the liner 15 condition to be assessed. For this test, the flange 27 is taped at 19a to enclose any permeating vapors which escape, through perforated vent plates 35, into the sample space 19. The probe 38 is inserted through the tape 19a to sample the gasses within sampling space 19.

FIG. 3 is a schematic sectional view of a fragmentary portion of two lined pipes 17 flanged together and where the vent for the annular space 13 is via vent holes 21 in the containing pipe 17. The drawing illustrates the use of the same gas detector 14 for measuring the mass flow $Q_m$ of gas permeating through the liner 15 via a sample from the vent hole 21.

We now compare the actual measured flow of gas $Q_m$ through the pipe liner against the expected value of $Q_m$ through a non-defective liner (as measured on a liner material sample in the laboratory). This data allows the condition of the liner to be assessed according to an appropriate acceptance/rejection criteria. Data from Example 1 indicates that a factor of 10 to 100 times normal permeation may be an appropriate value for this criterion.

EXAMPLE 1

Tracer Gas Injection

An experiment was conducted to demonstrate the effectiveness of the permeation test method to identify various service-related defects in PTFE-lined pipe. Helium was used as a tracer gas by injecting it into the process side of the lined pipe. First, the helium permeation characteristics were measured in virgin PTFE liners. FIG. 5 shows the characteristic response of helium in two different types of liners, molded and extruded. The permeability is related to the steady state flow rate and in this case is approximately equal to $1.3 \times 10^{-12}$ std. $cm^3 * cm/cm^2/sec/Pa$ at 95° F. for both liners.

For the field inspection of lined pipe, the dimensions of each pipe and liner are recorded so that the expected, or allowable, permeability and flange leakage are computed for each spool. Twenty pipes, some with known defects, were lined-up and used for the helium tracer permeation study by filling them with 1 percent helium as the tracer gas. Then, vent holes (FIG. 3) and taped flanges (FIG. 4) for all pipes and fittings were sampled for the presence of helium. For helium permeation and flange emission measurements, a Veeco MS20 Helium Mass Spectrometer was used. Spool vents and taped flanges were sampled with the sampling probe 38 capable of sampling up to 300 feet from the control unit. A reference leak with a National Institute of Standards and Technology (NIST) traceable helium leak rate of $3 \times 10^{-8}$ std. $cm^3$/sec was used to calibrate the sensitivity of the probe. The system sensitivity was $1 \times 10^{-5}$ std. $cm^3$/sec.

Four representative helium mass flow curves as a function of time were obtained as shown in FIG. 6. The top curve 6a was obtained from a pipe with a liner which had a pinhole-size leak. It is observed that the helium leaking through the pinhole gives a very fast response and a high helium indication. The lowest curve 6d is the permeation response from a pipe liner with no defects. Here the steady state level of permeation is almost four orders of magnitude below that of the real leak rate (curve 6a) and at least one hour is required to establish this steady state level. Not only the magnitude of observed helium flow rate but also the response time is significant. Thus, the invention provides a sensitive inspection technique because there are about four orders of magnitude difference between normal permeation rate (curve 6d) and a real leak rate (curve 6a) from a pinhole. The two middle curves 6b and 6c in FIG. 6 were obtained from pipes that permeated more than would have been expected from normal permeation. The second curve from the bottom 6c was from a lined pipe in which the liner was actually timed in certain places. The third curve from the bottom 6b was from a lined pipe in which the liner had blistered in service. These two defective liners exhibited an irregular "onset characteristic" (the time to establish initial permeation) and also exhibited a higher than expected helium permeation rate. FIG. 6 suggests that a factor of 10 to 100 times normal permeation rate may be used as a rejection criterion for defective lined pipe.

EXAMPLE 2

Process Gas Permeation

A suitable process stream which contains a volatile gas that is not present in the atmosphere, and which does not react with the atmosphere, may be used for on-line permeation testing without injection of a tracer. An elevated process temperature is also desirable to accelerate the permeation activity. The process that will be discussed in this example contained about ten mole percentage of propane.

Prior to field testing, the characteristic permeability coefficient P for propane in the liner material was measured in the laboratory using the setup of FIG. 2 with the chamber 28 connected to the test connection 26. A ⅛-inch thick molded PTFE slab of the liner material was subjected to propane permeation characterization. The sample was tested by mounting it in a thermally controlled chamber 28. A pure propane blanket at two atmospheres absolute pressure was introduced on one side of the liner material and a vacuum was introduced to the other side. A turbo-molecular pump 16 was used to create the vacuum and a mass spectrometer 14 was used to measure the propane permeating through the membrane 28a. FIG. 7 shows the characteristic permeation behavior that was observed for propane diffusing through the PTFE liner material at 174° F. Even though the test was being conducted at elevated temperature, steady state conditions were not achieved even after six days.

A steady state permeability coefficient for propane may be estimated by evaluating the product of its diffusivity D and solubility S. The computed diffusivity at 174° F. is $3 \times 10^{-8}$ cm²/sec. The estimated solubility S of propane in PTFE is $1.3 \times 10^{-6}$ std. cm³/cm³/Pa. Thus, the propane permeability P in PTFE is estimated to be $4 \times 10^{-14}$ std. cm³*cm/cm²/sec/Pa at 174° F.

For the pipe to be inspected in the field, the dimensions of each pipe and liner are recorded such that the expected, or allowable, permeability and flange leakage are computed for each spool. Then vent holes (per FIG. 3) and taped flanges (per FIG. 4) for all pipes and fittings are sampled for the presence of propane. For propane permeation and flange emission measurement, an Inficon quadruple mass spectrometer was used. A sampling probe 38 was used for sampling gasses and the probe was calibrated in a similar manner to that described for the helium test in Example 1.

The process line chosen for field inspection by process vapor permeation has normal operating conditions of approximately ten percent propane at 174° F. and 70 psig. The spools range in age from approximately a few months to 10 years or more. As such, various products from various vendors were present in the lines. None of the spools were leaking product at the time the line was tested. Using the propane flange emission and liner permeation detection techniques as previously described, 347 lined pipe spools and fittings totaling 499 feet and up to 12-inch diameter were inspected.

Of the spools tested, approximately one percent exhibited greater than 100 times normal permeation. Another one percent of the spools exhibited between 50 and 100 times normal permeation and about three percent exhibited between 15 and 50 times normal permeation.

We claim:

1. A nondestructive method for detecting a defective polymeric liner that is contained within, but is not bonded to, a vented structural shell wherein said liner does not exhibit a viscous leak, comprising the steps of:
    obtaining characteristic solute permeation data with respect to time at a given temperature on virgin polymers under laboratory conditions using a volatile tracer or process gas;
    introducing into the process side of said polymeric liner of said vented structural shell said solute as a tracer or process gas which will permeate through said polymeric liner and into the annulus formed between said liner and said vented structural shell;
    detecting the mass flow rate of said solute permeation with respect to time at said temperature at a vent location or flange of said vented structural shell with a suitable gas analyzer; and
    determining the mass flow rate of excess permeation with respect to time of said volatile solute through said polymeric liner by comparing said detected solute excess permeation data with respect to time with said characteristic solute permeation data with respect to time obtained from said virgin polymer.

2. The method of claim 1, wherein said mass flow rate of excess permeation of said volatile solute through said polymeric liner is at least a factor of ten (10) times, but not greater than a factor of ten thousand (10,000) times, the mass flow rate attributable to normal permeation of said volatile solute through said polymeric liner in its virgin condition.

3. The method of claim 1, wherein said mass flow rate of excess permeation of said volatile solute through said polymeric liner is directly proportional to the difference in partial pressure of said volatile solute on each side of said polymeric liner.

4. The method of claim 1, wherein said mass flow rate of excess permeation of said volatile solute through said polymeric liner increases exponentially with the temperature of said polymeric liner.

5. The method of claim 1, wherein said mass flow rate of excess permeation of said volatile solute through said polymeric liner requires a finite time to reach a steady state flow condition.

6. The method of claim 1, wherein said vented structural shell is constructed of a metallic pipe or vessel whose annular space between said structural shell and said polymeric liner is vented.

7. The method of claim 1, wherein said vented structural shell is constructed of a fiber-reinforced plastic pipe or vessel whose annular space between said structural shell and said polymeric liner is vented.

8. The method of claim 1, wherein said polymeric liner is selected from a group comprising: polytetrafluoroethylene, fluorinatedethylenepropylene polyvinylidene fluoride, polyvinylidenechloride, polyvinylchloride, polyethylene and polypropylene.

9. The method of claim 1, wherein said volatile solute is introduced into the process side of said polymeric liner and is detected at an annulus vent or flange location in said vented structural shell.

10. The method of claim 9, wherein said volatile solute is selected from a group comprising: helium, hydrogen, neon, argon, methane, ethane, ethylene, acetylene, propane, propylene and sulfur hexafluoride.

11. The method of claim 1, wherein said volatile solute is a component from a process in normal operation of said polymer lined, vented structural shell and is detected at an annulus vent or flange location.

12. The method of claim 1, wherein said non-leaking defect in said polymeric liner is wall thinning.

13. The method of claim 1, wherein said non-leaking defect in said polymeric liner is a blister.

14. The method of claim 1, wherein said measurement device is an analytical mass spectrometer.

* * * * *